United States Patent

Freitag

[11] Patent Number: 5,814,063
[45] Date of Patent: Sep. 29, 1998

[54] STENT FOR PLACEMENT IN A BODY TUBE

[75] Inventor: Lutz Freitag, Hemer, Germany

[73] Assignee: Willy Rusch AG, Kernen, Germany

[21] Appl. No.: 758,216

[22] Filed: Nov. 27, 1996

Related U.S. Application Data

[63] Continuation of Ser. No. 517,023, Aug. 18, 1995.

[30] Foreign Application Priority Data

Dec. 23, 1994 [DE] Germany .................... 44 46 036.8

[51] Int. Cl.⁶ .................................................. A61M 29/00
[52] U.S. Cl. ..................... 606/198; 606/191; 606/194; 606/200; 623/1; 623/12
[58] Field of Search ..................... 606/191, 194, 606/195, 198, 200; 623/1, 12

[56] References Cited

U.S. PATENT DOCUMENTS

| | | | |
|---|---|---|---|
| 4,503,569 | 3/1985 | Dotter | 623/1 |
| 4,731,073 | 3/1988 | Robinson | 623/1 |
| 5,064,435 | 11/1991 | Porter . | |
| 5,250,070 | 10/1993 | Parodi | 606/194 |
| 5,314,472 | 5/1994 | Fontaine | 623/12 |
| 5,397,355 | 3/1995 | Marin et al. | 623/12 |
| 5,665,115 | 9/1997 | Cragg | 623/1 |

FOREIGN PATENT DOCUMENTS

| | | |
|---|---|---|
| 0587197 | 3/1994 | European Pat. Off. . |
| 4102550 | 8/1991 | Germany . |
| 4219949 | 12/1993 | Germany . |
| 4301181 | 7/1994 | Germany . |

*Primary Examiner*—Michael Powell Buiz
*Assistant Examiner*—Daphna Shai
*Attorney, Agent, or Firm*—Friedrich Kueffner

[57] ABSTRACT

A stent for placement in a body tube includes a flexible support structure which is embedded in a hollow cylindrical casing of a synthetic material which at least at body temperature has limited elasticity. The support structure of the stent is composed of at least two zigzag-shaped wires which extend parallel to the longitudinal axis of the casing of the stent and which are offset relative to each other on the circumference of the casing, wherein each wire has at least three legs and the middle leg includes an acute angle with each of the two adjoining legs.

15 Claims, 5 Drawing Sheets

STENT FOR PLACEMENT IN A BODY TUBE

This is a continuation of application Ser. No. 08/517,023 filed Aug. 18, 1995.

BACKGROUND OF THE INVENTION

1. Field of the Invention

The present invention relates to a stent for placement in a body tube including a flexible support structure which is embedded in a hollow cylindrical casing of a synthetic material which at least at body temperature has limited elasticity.

2. Description of the Related Art

Stents of this type are used in the treatment of stenoses. A stenosis is a congenital or acquired constriction in a body tube. It may occur in hollow organs, such as, trachea, esophagus, stomach and intestines or blood vessels and may occur as a result of illness through the formation of growths, inflammations with connective tissue tumors, or shrinking scars, through thrombosis or arterial sclerotic processes as well as through cauterization. Depending on the extent of the stenosis, the stenosis causes a partial blocking in the affected body tube or may even entirely close the body tube.

It is known to place so-called stents for expanding or keeping open stenoses, either in blood vessels or other hollow organs. The stents keep the vessel open as an internal support and, thus, act as spacer members.

Stents for keeping stenoses open are known in various embodiments. Stenoses are available in metal and/or synthetic material. They usually are composed of a braided member of metal wires which automatically expand as a result of their natural tension. However, there are also other stents which must be expanded into the expanded position at the place of use by means of a suitable device, for example, a balloon catheter.

Stents of so-called memory metal are known in the art from DE-OS 42 19 949 or DE-OS 43 01 181. At a low temperature, these stents have a small radial diameter. They are placed in the stenosis in this state. They expand radially when a limiting temperature which is below body temperature is exceeded, so that they can hold a stenosis open in this manner.

Moreover, it is known from EP-05 87 197 and DE-OS 41 02 550 to embed the supporting metal segments in a closed casing of base materials, for example, silicone, which are compatible with tissue, in order to prevent the stent from growing through tissue cells. However, the above-described embodiments have the disadvantage that, when radial pressure is applied to the stents, for example, by pressing the stent together before placement, the stents are elongated in axial direction and become shorter again when they expand. This phenomenon must be taken into consideration especially when planning the treatment of a stenosis because the stent must be adjusted very precisely. A subsequent adjustment or correction of the length in the body is not possible.

In the case of natural loads acting on the stent, such as a coughing process, a change in length can also be observed. This may lead to problems because it may cause relative movements between the stent and the wall of the body tube in which the stent is placed. Irritations of the tube wall or the surrounding tissue occur as a result. In addition, the relative movement may also lead to displacement of the stent.

U.S. Pat. No. 5,064,435 discloses a self-expanding stent which is supposed to ensure a stable axial length. However, this stent is relatively complicated in its construction. Consequently, this stent is difficult to manufacture and also difficult to use. Moreover, in this type of stent, there is the danger that tissue cells grow through the mesh grid, which may lead to a renewed partial or complete closure of the vessel.

Thus, there are a number of stents which meet the requirements made of the stents differently depending on the case of application. However, there is still the need to further develop and improve the stents. Especially the construction of the braided or woven member of metal wires which forms the support structure of a stent is considered to be too complicated and too disadvantageous.

SUMMARY OF THE INVENTION

Therefore, it is the primary object of the present invention to provide a stent of the above-described type which is of simple construction, in which especially the danger of growth of tissue cells through the stent is avoided and which ensures a gentle placement of the stent in the body tube.

In accordance with the present invention, the support structure of the stent is composed of at least two zigzag-shaped wires which extend parallel to the longitudinal axis of the casing of the stent and which are offset relative to each other on the circumference of the casing, wherein each wire has at least three legs and the middle leg includes an acute angle with each of the two adjoining legs.

Accordingly, the individual wires of the support structure have a tree-shaped configuration. A leg of the wire is connected to the next leg which extends in the opposite direction and forms an acute angle with the leg. The next leg is then also connected to the next following leg in such a way that they include an acute angle with each other.

The support structure formed of several wires which are arranged offset relative to each other is embedded in a casing composed of a synthetic material which is elastic at body temperature. The casing prevents tissue cells from growing through the support structure.

In its simplest form, an entire wire may be composed of only three legs. Because of the fact that the middle leg includes an acute angle with each of the two adjoining legs, the middle leg may be shorter than the two adjoining outer legs.

In accordance with an advantageous feature of the present invention, the legs of a wire are arranged in such a way that always two legs form an angle which is smaller than 45°. This geometric shape of the wires ensures a stability of the stent with respect to length. Even when the stent is pressed together, the length of the stent does not change. This is particularly important in the planning of the treatment of a stenosis because the stent can now be adjusted exactly to its required length.

When a pressure is applied radially from the outside on such a stent, the point of connection or bend between two legs is moved in a rotating movement toward the inside. However, the inner end of the leg is moved simultaneously with its bend in the opposite direction. As a result, the movements cancel each other out. The stent remains stable in its total length.

The stent remains stable with respect to its length even if a pressure is applied to a wire in a direction perpendicularly to the longitudinal axis of the leg. In that case, the wire bends toward the middle. The adjoining wires would then move away relatively from each other. However, this is prevented by the fact that the support structure is embedded in the elastic casing.

If a longitudinal stability of the stent is not required or not desired, another feature of the present invention provides that each angle between two adjoining legs is greater than or equal to 45° and smaller than or equal to 90°.

Such a stent has a uniform restoring force at the circumference thereof. The stent is uncomplicated in its construction and can be easily manufactured. The stent also provides advantages with respect to standardization which must be adapted to each stenosis; this is because the stent can be easily cut to the required length.

In accordance with another feature of the present invention, two wires arranged next to each other on the circumference of the casing engage in each other in a toothing-like manner. This supports the restoring force of the stent on the circumference thereof. In accordance with this feature, always two tips formed by two legs of a wire overlap each other by a certain dimension, such that the tips of one wire engage in the valleys of the other wire. However, the wires do not contact each other. As a result, an effective co-operation of the support structure with the casing is ensured. When a pressure is applied to the stent, the legs move apart relatively from each other, so that a tensile stress is produced in the casing which causes the restoring process. Accordingly, the tensile force is transformed in the casing into a compressive force. This compressive force acts against the compressive force acting from the outside and, thus, produces a reaction force in the wires.

In accordance with another feature of the present invention, adjoining legs are connected to each other through rounded length portions. As a result, sharp edges are avoided which could lead to damage of the casing. Moreover, a wire can then be easily manufactured by bending by means of rounded shaping tools.

Another feature provides that projections are provided on the casing, wherein the projections are distributed over the circumference. This feature prevents displacement of the stent in the body tube. The projections may be arranged uniformly or irregularly distributed over the circumference.

It is basically conceivable to produce the projections in various ways, such as, by knobs, hooks or tips. However, in accordance with an advantageous embodiment of the invention, each projection is formed by length portions of the wires which connect two adjoining legs to each other and project beyond the circumference. As a result, radial abutments are formed which are distributed over the circumference of the stent and which ensure a stable position of the stent.

The abutments can be produced by having always two adjoining legs extend not plane-parallel to the outer circumference of the stent, but rather outwardly tilted or twisted relative to the outer circumference. Consequently, the stent has a surface which is not smooth and provided with projections. This configuration is gentler for the respective organ walls or vessel walls and also for the mucous membranes than would be a circular anchoring. In that case, the surface has an irregularly corrugated structure. This prevents blood vessels on the circumference of the stents from being tied up or pressed against. Consequently, a better blood supply in the outer blood vessel is ensured.

The abutment structure of the wire can be provided on the entire length thereof. However, it is also conceivable to provide the projections only at some of the legs.

Another possibility for providing a stent with projections is to have the wires of the support structure protrude with the ends thereof beyond the casing and/or additionally deform the ends. In this manner, projections in the form of claws at the ends of the wires can be formed.

In accordance with another feature, the wires are of metal. Any metal which meets medical requirements can be used.

It is conceivable that the wires are of steel and the casing of an elastomer. The steel must be a stainless steel. Stainless steel is inexpensive and also simple to process. The natural tension inherent in the steel supports the self-expanding effect of the stent. The material of the casing is preferably silicone. However, other types of synthetic rubber can also be used if they meet medical requirements, particularly with respect to tissue compatibility and freedom from allergies. The selection of the elastomer makes it possible to more or less strongly adjust the circumferential restoring forces of the stent.

For the placement of the stent, an appropriate tool is required. The tool holds the stent together when the stent is inserted. For the placement, the stent is released by the tool and expands into its expanded position solely by the internal tension inherent in the material.

However, the wires of the stent can also be of a memory metal. Such a memory metal is a shape memory alloy. Such alloys are usually formed from a combination of the two metals nickel and titanium (nitinol).

A shape memory alloy has a compressed structure at a low temperature. However, this material expands when a limiting temperature is exceeded. The desired limiting conditions can be adjusted by an appropriate selection of the alloy components.

The material for the casing is an elastomer which has a low tensile force, for example, latex. The casing must permit the expansion of the memory metal wires and must ensure such an elasticity after the expansion that a collapse of the entire structure is prevented. Consequently, the elastomer effects the sufficient stabilization of the wires.

An insertion tool is also required for this combination.

In accordance with an advantageous embodiment of the invention, the casing is of a memory elastomer. This is a temperature-dependent elastomer or shape memory polyurethane which is hard and small in the cold state. Consequently, the stent can be inserted without problems. The spacer member expands only at body temperature or slightly below body temperature.

The combination of a memory elastomer as the casing with a support structure of wires of a memory metal is considered particularly advantageous. The wires of memory metal or nitinol are soft at room temperature. On the other hand, a shape memory polyurethane is hard. The combination results in a small tube which is thin and hard at room temperature. At body temperature, the shape memory polyurethane becomes soft and flexible, while the support structure of nitinol expands. The result is a stent which is thick and hard, but elastic.

An insertion tool is not required for such a stent because the stent is hard and small in the cold state. Accordingly, the stent can be inserted without problems. A contributing factor in this connection is the fact that nitinol is deformable, i.e., plastically soft, in the cold state.

The stent is manufactured by combining the memory metal in a state in which it is still soft and deformable with the memory elastomer which is already in the soft state. Thus, the support structure is cast in a narrow, small state into the elastomer. The manufacturing process is carried out in a temperature range in which the two materials have not yet changed their body states.

It is basically also conceivable that the wires forming the support structure are of synthetic material. Suitable synthetic materials which have the desired stability and ensure the restoring force for the stent are available for this purpose. The wires of synthetic material can also be embedded in a casing which is composed of a memory elastomer.

In accordance with another advantageous feature of the present invention, the wires of the support structure have intended bending points. This also makes it possible to provide a stent which has stability with respect to length. For example, if an external force is applied perpendicularly onto the tip formed by two adjoining legs, this results in a bending of the legs. However, the respectively other ends of the legs remain stable with respect to their positions, i.e., they are not displaced in axial direction of the stent. Accordingly, the stent remains constant with respect to its total length. The restoring process of the legs is effected by the springy properties of the wire which is supported by the elastic properties of the casing.

The intended bending points according to the invention may be produced, for example, by providing decreased thickness portions or notches in the wires at suitable locations. However, it is also possible to produce the intended bending points by combining two or more different materials in the wires.

The various features of novelty which characterize the invention are pointed out with particularity in the claims annexed to and forming a part of the disclosure. For a better understanding of the invention, its operating advantages, specific objects attained by its use, reference should be had to the drawing and descriptive manner in which there are illustrated and described preferred embodiments of the invention.

DESCRIPTION OF THE PREFERRED EMBODIMENTS

Figure 1:
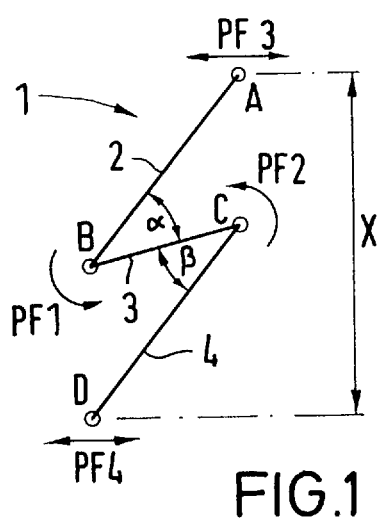
FIG. 1 is a schematic side view of a wire with three legs, showing the sequence of movements of the wire.

FIG. 1 of the drawing shows three legs 2, 3, 4 of a wire 1. The middle leg 3 includes with each of the two adjoining legs 2 and 4 an acute angle α, β, respectively, of 35°.

The end points tips between the legs are denoted by letters A to D.

When pressure is applied radially from the outside on the tip B and the end points A and D are considered fixed, the tip B moves in a rotating movement indicated by PF1 in the plane of the drawing toward the bottom and inside. Simultaneously, the inner tip C moves in an opposite movement denoted by PF2 toward the outside and up. The movements are superimposed on each other and, thus, cancel each other out. Consequently, the total length X of wire 1 remains constant. The end points A and D can move radially in the directions PF3 and PF4 without being subject to axial displacement.

When a force directed perpendicularly into the plane of the drawing acts on the wire 1, the wire 1 bends perpendicularly to its longitudinal axis.

As a result of the above-described relationships, a longitudinal stability of the stent can be ensured. A stent, whose support structure is composed of the zigzag-shaped wires of the configuration shown in FIG. 1, remains stable in its total length, even when it is compressed.

Figure 2:
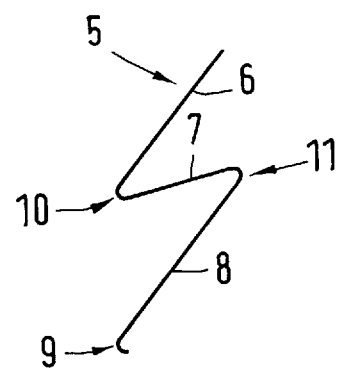
FIG. 2 is a side view of a wire according to the present invention with rounded tips.

FIG. 2 of the drawing shows a portion of a wire 5 whose legs 6, 7, 8 are connected to each other through rounded length portions 9, 10 and 11.

FIGS. 3a–3g show different configurations of wires 12–18. All wires 12–18 have in common that the legs include acute angles with each other.

The angles γ', γ" of the wires 12, 13, 14 and 17 are all smaller than 45°. On the other hand, the angles δ', δ" of the wires 15 and 16 are greater than 45°.

Figure 3A:
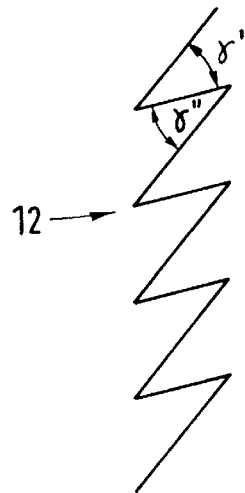
FIGS. 3a–3g are side views of seven different embodiments of wires.
Figure 3B:
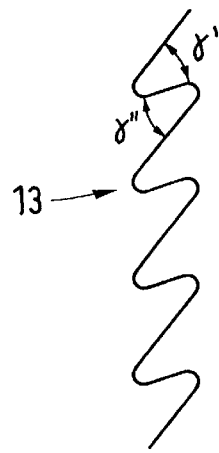
Figure 3C:
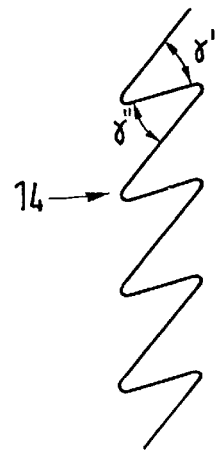
Figure 3D:
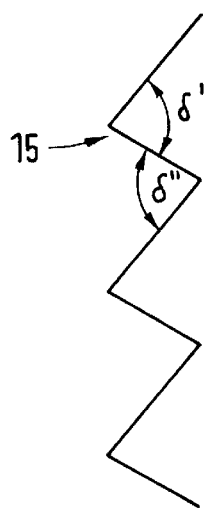
Figure 3E:
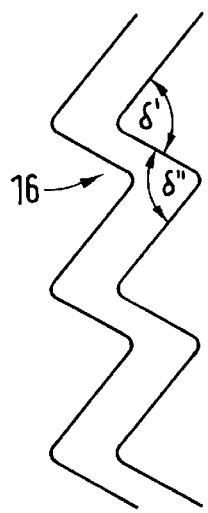
Figure 3F:
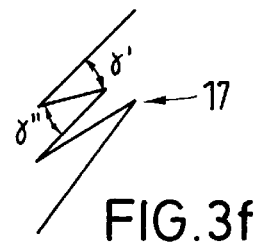
Figure 3G:
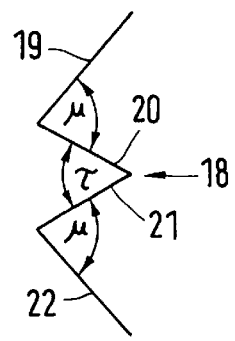

FIG. 3g shows a wire 18 with legs 19 to 22 in which the angle μ between the legs 19 and 20 and between legs 21 and 22 is greater than 45° while the angle τ between the legs 20 and 21 is smaller than 45°.

Figure 4:
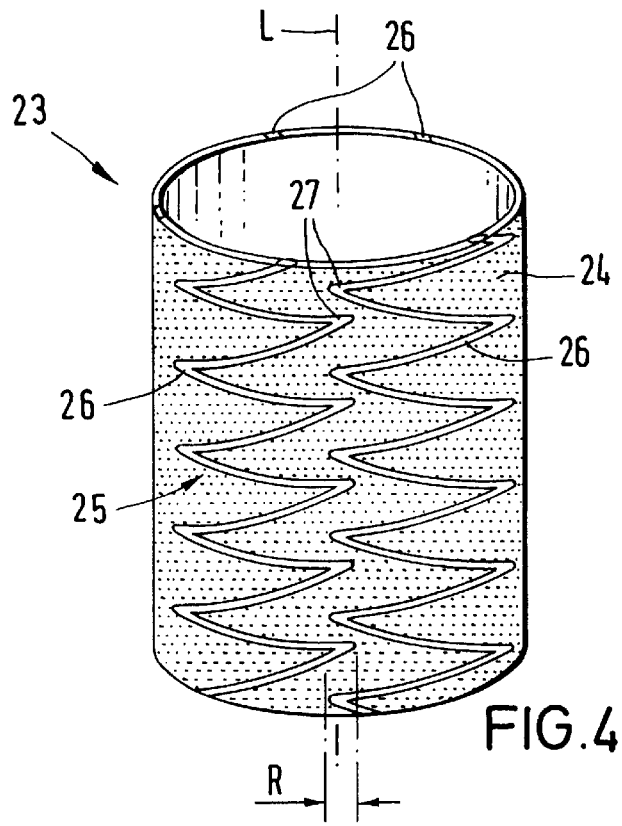
FIG. 4 is a perspective view of a stent according to the present invention.

FIG. 4 of the drawing shows a stent 23 with a hollow cylindrical casing 24. A support structure 25 is embedded in the casing 24. The support structure 25 is formed by the wires 26 which generally extend parallel to the longitudinal axis L of the casing 24 and are offset relative to each other.

The casing 24 is composed of an elastomer. Preferably, a memory elastomer is used. The wires 26 are of metal, wherein preferably a memory metal is used.

The individual wires 26 engage in each other in a toothing-like manner with the rounded length portions 27. This means that the length portions 27 overlap each other in the plane of the drawing by the dimension R.

Figures 5A, 5B:
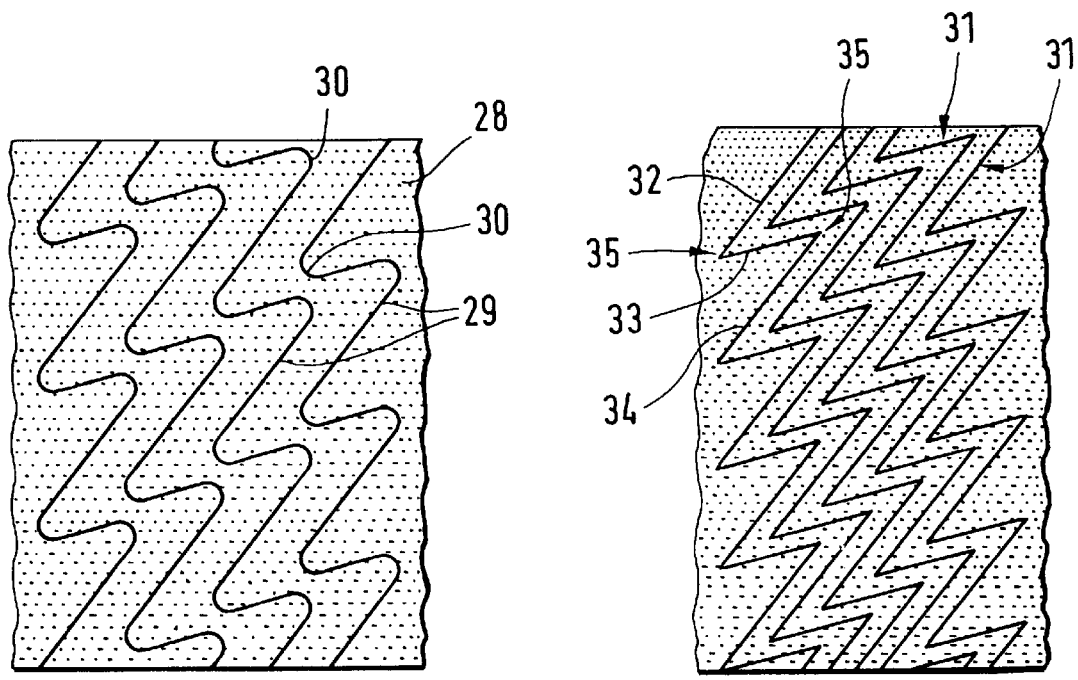
FIG. 5a is a partial developed view of a stent.
FIG. 5b is a developed view of another embodiment of the stent.

FIG. 5a shows a portion of a stent in which wires 29 with rounded length portions 30 are embedded in the casing 28. The wires 29 also engage in each other in a toothing-like manner.

A toothing-like engagement is also realized in the configuration of FIG. 5b. However, in this configuration of the wires 31, the individual legs 32, 33, 34 are connected to each other in sharp tips 35.

Figure 6:
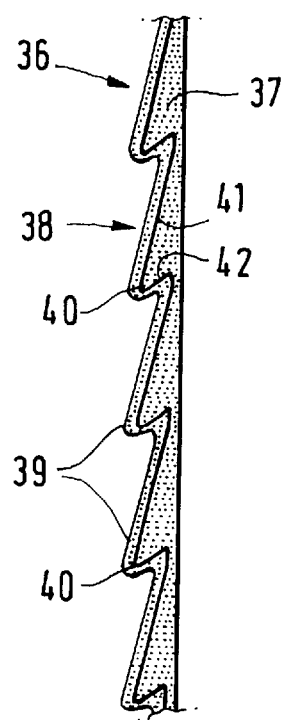
FIG. 6 is a vertical sectional view of the casing of a stent.
Figure 7:
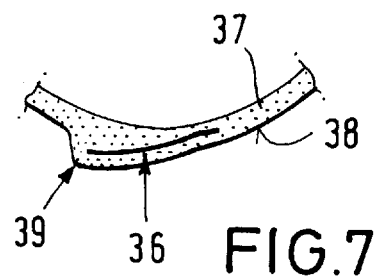
FIG. 7 is a partial sectional view of a stent.

FIGS. 6 and 7 show a wire 36 which forms projections 39 in the casing 37, wherein the projections 39 are distributed over the circumference 38. The bends 40 between the individual legs 41, 42 of the wire 36 are outwardly twisted over the circumference 38 in such a way that the projections 39 are formed so as to project out of the casing 37.

The projections 39 ensure a secure support of a stent after the stent has been mounted in a body tube.

Figures 8A, 8B:
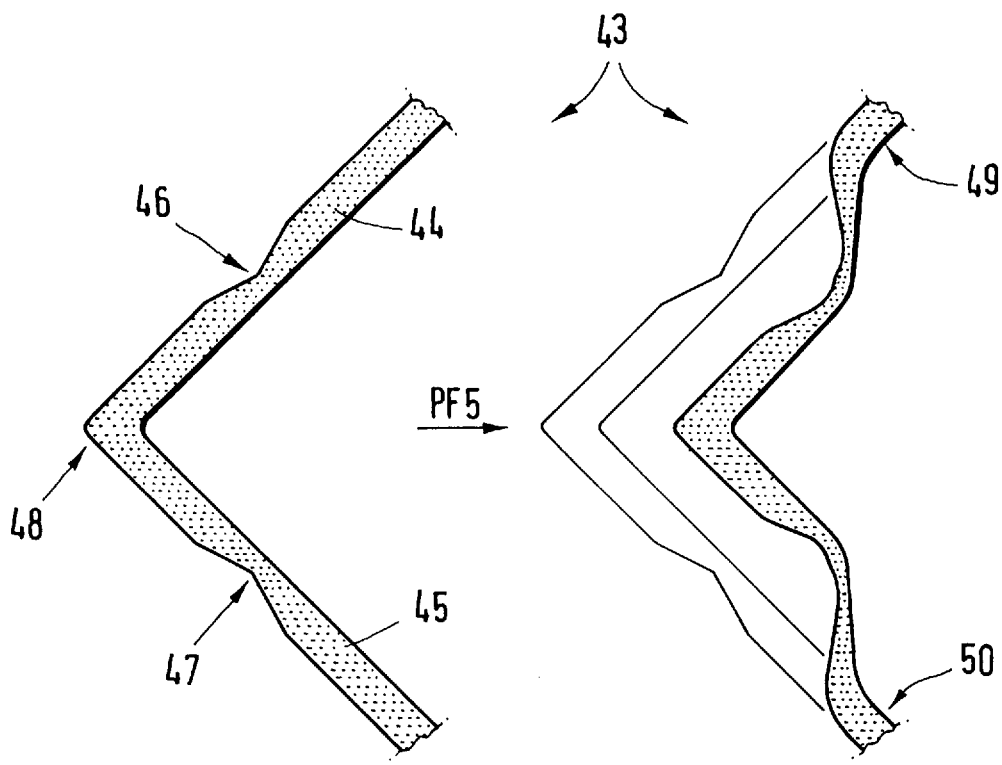
FIG. 8a is a partial sectional view, on a larger scale, of two legs of a wire with intended bending points.
FIG. 8b is a view of FIG. 8a in a bent position.

FIGS. 8a and 8b show a portion of a wire 43 with intended bending points 46, 47 integrated in the legs 44, 45. When a load is applied on the wire 43 from the direction indicated by PF5, the tip 48 between the two legs 44, 45 is displaced in the plane of the drawing toward the right while deforming the intended bending points 46, 47, without causing a displacement of the leg portions 49, 50. Consequently, the total length of the wire 43 in axial direction remains constant.

Figure 9:
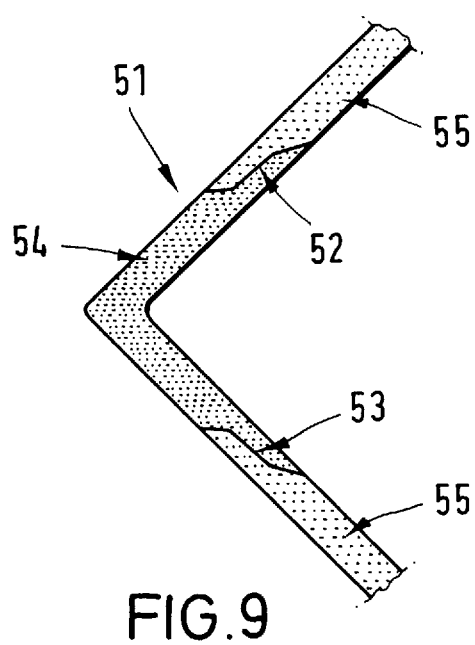
FIG. 9 is a partial sectional view of a wire composed of two different materials.

FIG. 9 of the drawing shows another embodiment of a wire 51 with intended bending points 52, 53. The wire 51 has portions 54, 55 which are of different materials. By combining the different materials having different material characteristics, the wire 51 has zones in which the wire 51 preferably bends when a load is applied.

The invention is not limited by the embodiments described above which are presented as examples only but can be modified in various ways within the scope of protection defined by the appended patent claims.

I claim:

1. A stent for placement in a body tube, the stent comprising a hollow cylindrical casing having a longitudinal axis, a flexible support structure embedded in the casing, the casing being of a synthetic material which is elastic to a limited extent at least at body temperature, the support structure comprising a plurality of zig-zag-shaped wires, the wires extending parallel to the longitudinal axis of the casing and being offset relative to each other in circumferential direction of the casing, wherein each wire has at least three legs including a middle leg and two adjoining legs, wherein the middle leg includes an acute angle with each of the adjoining legs, the two adjoining legs having outer ends and inner ends connected to the middle leg in points of connection, wherein the acute angle is smaller than 45°, whereby a pressure applied in radial direction causes the points of connection to be rotated and moved in opposite directions such that the movements cancel each other out while the outer ends remain stationary, so that a total length of each wire and of the stent remains constant in axial direction when a pressure is applied in radial direction.

2. The stent according to claim 1, wherein the at least two zig-zag-shaped wires form tips and valleys, and wherein the at least two wires engage each other in a toothing-like manner, such that the tips of one of the wires are located in the valleys of another of the wires.

3. The stent according to claim 1, comprising rounded length portions connecting the middle leg to the adjoining legs.

4. The stent according to claim 1, wherein the casing has a circumference, further comprising projections distributed over the circumference of the casing.

5. The stent according to claim 4, wherein each projection is formed by length portions which connect the middle leg to the adjoining legs and project beyond the circumference of the casing.

6. The stent according to claim 1, wherein the wires are of metal.

7. The stent according to claim 1, wherein the wires are of steel and the casing is of an elastomer.

8. The stent according to claim 7, wherein the elastomer is silicone.

9. The stent according to claim 1, wherein the wires are of a memory metal and the casing is of an elastomer.

10. The stent according to claim 9, wherein the memory metal is nitinol and the elastomer is latex.

11. The stent according to claim 1, wherein the wires are of nitinol and the casing is of polyurethane.

12. The stent according to claim 1, wherein the wires are of synthetic material.

13. The stent according to claim 1, wherein the wires are of synthetic material and the casing is of a memory elastomer.

14. The stent according to claim 1, wherein the wires have intended bending points.

15. A stent for placement in a body tube, the stent comprising a hollow cylindrical casing having a longitudinal axis, a flexible support structure embedded in the casing, the casing being of a memory elastomer material which is elastic to a limited extent at least at body temperature, the support structure comprising a plurality of zig-zag-shaped wires, the wires extending parallel to the longitudinal axis of the casing and being offset relative to each other in circumferential direction of the casing, wherein each wire has at least three legs including a middle leg and two adjoining legs, wherein the middle leg includes an acute angle with each of the adjoining legs, the two adjoining legs having outer ends and inner ends connected to the middle leg in points of connection, wherein the acute angle is smaller than 45°, whereby a pressure applied in radial direction causes the points of connection to be rotated and moved in opposite directions such that the movements cancel each other out while the outer ends remain stationary, so that a total length of each wire and of the stent remains constant in axial direction when a pressure is applied in radial direction.

* * * * *